(12) United States Patent
Beckman et al.

(10) Patent No.: US 7,895,725 B2
(45) Date of Patent: Mar. 1, 2011

(54) METHOD OF MANUFACTURING A NEEDLE ASSEMBLY FOR USE WITH A BIOPSY DEVICE

(75) Inventors: Andrew T. Beckman, Cincinnati, OH (US); Noreen Kascak, Cincinnati, OH (US); Lee Reichel, Springboro, OH (US); Michael Ludzack, Maineville, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

(21) Appl. No.: 12/437,961

(22) Filed: May 8, 2009

(65) Prior Publication Data
US 2009/0260755 A1  Oct. 22, 2009

Related U.S. Application Data

(62) Division of application No. 11/027,120, filed on Dec. 30, 2004, now abandoned.

(51) Int. Cl.
*B23P 25/00* (2006.01)
*B05D 3/00* (2006.01)
(52) U.S. Cl. .......................................... 29/458; 427/2.12
(58) Field of Classification Search ............ 29/898.057, 29/898.056, 898.055, 898.049, 898.048, 29/458, 428; 156/245, 252; 264/328.1; 600/564–567, 562, 563, 167, 170; 427/2.12
See application file for complete search history.

(56) References Cited

U.S. PATENT DOCUMENTS

| 3,844,272 A | 10/1974 | Banko |
| 5,526,822 A | 6/1996 | Burbank et al. |

(Continued)

FOREIGN PATENT DOCUMENTS

WO  WO 02/062231  8/2002

OTHER PUBLICATIONS

U.S. Appl. No. 08/825,899, filed Apr. 2, 1997, Ritchart et al.

(Continued)

*Primary Examiner* — John C Hong
(74) *Attorney, Agent, or Firm* — Frost Brown Todd LLC

(57) ABSTRACT

An improved process for manufacturing a biopsy needle assembly is provided. The process may comprise the steps of forming an aperture for receiving tissue to be sampled in an exterior surface of an elongated tube for receiving a cutter, wherein the elongated tube comprises a proximal portion and a distal portion; forming a hole in the exterior surface of the elongated tube; and applying a coating of material over the elongated tube to form a lumen for receiving vacuum on the exterior surface of the elongated tube, wherein the hole in the exterior surface of the elongated tube provides communication between an interior of the elongated tube and an interior of the lumen. In one version, the elongated tube may be placed in a mold configured to form the vacuum lumen when material is injected into the mold. A proximal hub may advantageously be formed by overmolding.

18 Claims, 6 Drawing Sheets

U.S. PATENT DOCUMENTS

| | | | |
|---|---|---|---|
| 5,649,547 | A | 7/1997 | Ritchart et al. |
| 5,895,401 | A | 4/1999 | Daum et al. |
| 6,086,544 | A | 7/2000 | Hibner et al. |
| 6,436,054 | B1 | 8/2002 | Viola et al. |
| 6,485,436 | B1 | 11/2002 | Truckai et al. |
| 6,620,111 | B2 | 9/2003 | Stephens et al. |
| 6,626,849 | B2 | 9/2003 | Huitema et al. |
| 6,638,235 | B2 | 10/2003 | Miller et al. |
| 7,189,207 | B2 | 3/2007 | Viola |
| 7,445,739 | B2 | 11/2008 | Tsonton et al. |
| 2002/0120212 | A1 | 8/2002 | Ritchart et al. |
| 2003/0109803 | A1* | 6/2003 | Huitema et al. ............ 600/564 |
| 2003/0199753 | A1 | 10/2003 | Hibner et al. |
| 2003/0199754 | A1 | 10/2003 | Hibner et al. |
| 2003/0199785 | A1 | 10/2003 | Hibner et al. |
| 2005/0212175 | A1* | 9/2005 | Tsonton et al. ............ 264/328.1 |
| 2006/0144549 | A1 | 7/2006 | Beckman et al. |

OTHER PUBLICATIONS

European Search Report and Search Opinion of the European Patent Office dated Mar. 24, 2006 for Application No. EP 05 25 8094.

* cited by examiner

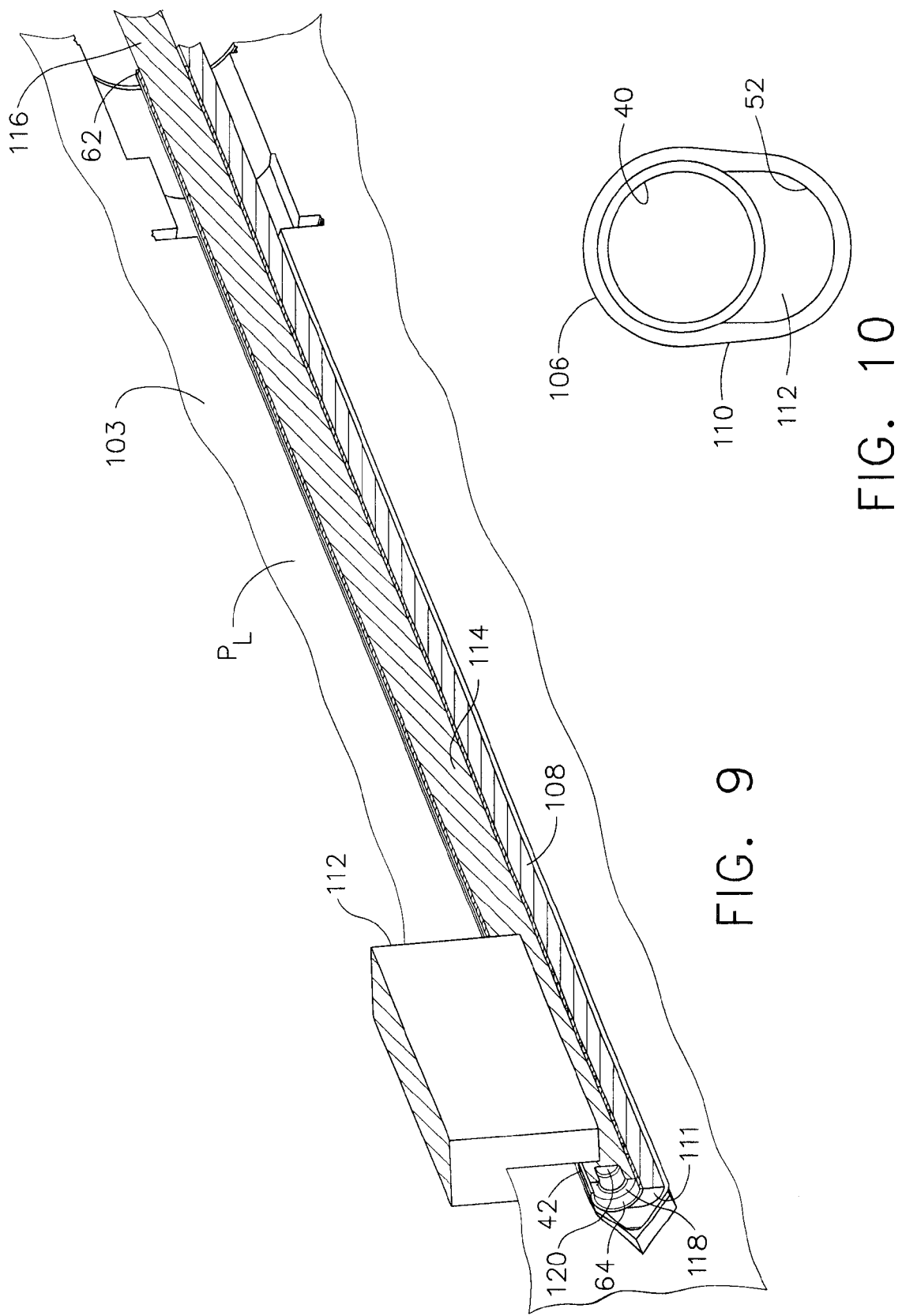

METHOD OF MANUFACTURING A NEEDLE ASSEMBLY FOR USE WITH A BIOPSY DEVICE

This application is a divisional of U.S. Non-Provisional patent application Ser. No. 11/027,120, entitled "Method of Manufacturing a Needle Assembly for Use with a Biopsy Device," filed Dec. 30, 2004, the disclosure of which is incorporated by reference herein.

FIELD OF THE INVENTION

The present invention is related generally to biopsy devices and, more particularly, to an improved process of manufacturing a needle assembly for use with a biopsy device for acquiring a tissue sample.

BACKGROUND OF THE INVENTION

The diagnosis and treatment of patients with cancerous tumors, pre-malignant conditions, and other disorders has long been an area of intense investigation. Non-invasive methods for examining tissue include palpation, thermography, PET, SPECT, Nuclear imaging, X-ray, MRI, CT, and ultrasound imaging. When the physician suspects that tissue may contain cancerous cells, a biopsy may be done either in an open procedure or in a percutaneous procedure. For an open procedure, a scalpel is used by the surgeon to create a large incision in the tissue in order to provide direct viewing and access to the tissue mass of interest. Removal of the entire mass (excisional biopsy) or a part of the mass (incisional biopsy) is performed. For a percutaneous biopsy, a needle-like instrument is inserted through a very small incision to access the tissue mass of interest and to obtain a tissue sample for later examination and analysis.

The advantages of the percutaneous method as compared to the open method are significant: less recovery time for the patient, less pain, less surgical time, lower cost, less risk of injury to adjacent bodily tissues such as nerves, and less disfigurement of the patient's anatomy.

Generally there are two ways to percutaneously obtain a portion of tissue from within the body: aspiration and core sampling. Aspiration of the tissue through a fine needle requires the tissue to be fragmented into pieces small enough to be withdrawn in a fluid medium. This method is less intrusive than other known sampling techniques, but one may only examine cells in the liquid (cytology) and not the cells and the structure (pathology). In core sampling, a core or fragment of tissue is obtained for histologic examination and/or genetic tests, which may be done via a frozen or paraffin section. The type of biopsy used depends mainly on various factors present in the patient, and no single procedure is ideal for all cases. However, core biopsies seem to be more widely used by physicians.

The following patent documents are incorporated herein by reference for the purpose of illustrating biopsy devices and methods: U.S. Pat. No. 5,526,822 issued Jun. 18, 1996; U.S. Pat. No. 5,895,401 issued Apr. 20, 1999; U.S. Pat. No. 6,086,544 issued Jul. 11, 2000; U.S. Pat. No. 6,620,111 issued Sep. 16, 2003; U.S. Pat. No. 6,626,849 issued Sep. 30, 2003; U.S. Pat. No. 6,638,235 issued Oct. 28, 2003; US patent application Ser. No. 2003/0109803 published Jun. 12, 2003; US patent application Ser. No. 2003/0199753 published Oct. 23, 2003; US patent application Ser. No. 2003/0199754 published Oct. 23, 2003; US patent application Ser. No. 2003/0199785 published Oct. 23, 2003; and U.S. Ser. No. 08/825,899 filed on Apr. 2, 1997.

It is known in the art to use a double lumen biopsy needle incorporating vacuum suction to obtain a tissue sample. With devices of this type, the needle is inserted into a small incision in a patient and is advanced through tissue until the needle is adjacent the tissue of interest. At that point, a vacuum source may be activated, providing suction inside one of the two lumens. The suction is communicated to the second lumen via a passage between the two lumens. The second lumen may contain an aperture through which suspicious tissue may be drawn when the vacuum source is activated. Once tissue is drawn into the aperture, the surgeon may advance a cutter through the second lumen in order to excise a sample from the tissue of interest.

While biopsy needles of the type described above are useful in obtaining tissue samples, the processes known in the art for manufacturing these needles are often expensive and labor-intensive due to the number of components and steps involved. For instance, certain biopsy needles provide a double lumen structure formed of two separate rigid structures, thus requiring a reliable method of attaching the two structures, such as a weld or adhesive, along the entire length of the lumens. Similarly, many biopsy needles include a sharpened feature on the leading end of the needle that cuts through tissue as the needle is advanced into the body. These sharpened tips often have small components and/or features that require significant time and expense to make and attach to the needle. Further, biopsy needles often include a mounting component that allows the needle to be attached to a handle or other platform. Often, these mounting components are manufactured separately from the body of the needle, and must be joined together after formation, such as by gluing, a process that is heavily reliant on the skill and concentration of a human worker. Even if a more reliable method of attaching the mounting component to the needle is used, such as induction heating or heat staking, such methods still involve the added expense necessitated by the extra assembly equipment as well as the steps of manufacturing the mounting component and attaching it to the needle.

Accordingly, while double lumen biopsy needles are known in the art, there exists a significant need for a process of manufacturing a biopsy needle that reduces the number of components that must be separately manufactured, as well as the time and labor that must be expended in manufacturing and assembling the components of the biopsy needle, while still maintaining the necessary strength and rigidity for safe and satisfactory performance during surgery.

SUMMARY OF THE INVENTION

The process of the current invention overcomes the above-noted and other deficiencies of the prior art by providing a process for manufacturing a biopsy needle device that reduces the number of components that must be separately manufactured and assembled, thereby reducing the cost of manufacturing the biopsy needle device while maintaining the necessary biomechanical properties.

In one aspect consistent with the present invention, a process of manufacturing a biopsy needle may comprise the steps of forming an aperture for receiving tissue to be sampled in an exterior surface of an elongated tube that has a proximal and distal portion, wherein the elongated tube may be configured to receive a cutter; forming a hole in the exterior surface of the elongated tube; and applying a coating of material over the elongated tube to form a lumen for receiving vacuum on the exterior surface of the elongated tube, wherein the hole in the exterior surface of the elongated tube may be adapted to provide communication between an interior of the elongated tube and an interior of the lumen. This process advantageously allows the vacuum lumen to be formed over the elongated tube without requiring separate manufacturing and assembly steps, thus reducing assembly costs.

In another version, the process of manufacturing the biopsy needle device may comprise the steps of forming an aperture for receiving tissue to be sampled in an exterior surface of an elongated tube, wherein the elongated tube may be adapted to receive a cutter and may further comprise a proximal portion and a distal portion; forming a hole in the exterior surface of the elongated tube; and placing the elongated tube in a mold and injecting the mold with a material, wherein the mold may be configured such that the material forms a lumen for receiving vacuum on the exterior surface of the elongated tube, and wherein further the hole in the exterior surface of the elongated tube may be adapted to provide communication between an interior of the elongated tube and the interior of the lumen. This version advantageously provides for the formation of a vacuum lumen on an elongated tube by overmolding a coating of material onto the elongated tube, avoiding the need to separately manufacture the vacuum lumen and then attach it to the elongated tube. Further, this process may provide for a stronger attachment between the vacuum lumen and the elongated tube than some previously known methods of attachment of the two components.

In another aspect, the process of manufacturing a biopsy needle device may comprise the steps of placing a cutter tube, which may comprise a port adapted to receive a tissue sample and may further comprise a cutter lumen adapted to receive a cutter, in a mold; injecting a material in a liquid state into the mold; cooling the material in order to convert it to a solid state; wherein the mold may be configured to cause the material to form a lumen for receiving vacuum on an exterior surface of the cutter tube, and wherein further the vacuum lumen is in communication with the cutter lumen.

The present invention also extends to a biopsy instrument manufactured according to a process that may comprise the steps of forming an aperture for receiving tissue to be sampled in an exterior surface of an elongated tube for receiving a cutter, wherein the elongated tube may have a proximal portion and a distal portion; forming a hole in the exterior surface of the elongated tube; and applying a coating of material over the elongated tube to form a lumen for receiving vacuum on the exterior surface of the elongated tube, and wherein the hole in the exterior surface of the elongated tube may be adapted to provide communication between an interior of the elongated tube and an interior of the lumen.

These and other objects and advantages of the process of the present invention shall be made apparent from the accompanying drawings and the description thereof.

BRIEF DESCRIPTION OF THE DRAWINGS

The novel features and steps of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 9 is an isometric view of a right half of a needle assembly mold with slides in place for use in injection molding according to one version of the process.

FIG. 10 is a partial frontal cross-sectional view of a needle assembly manufactured according to one version of the process.

DETAILED DESCRIPTION OF THE INVENTION

Figure 1:
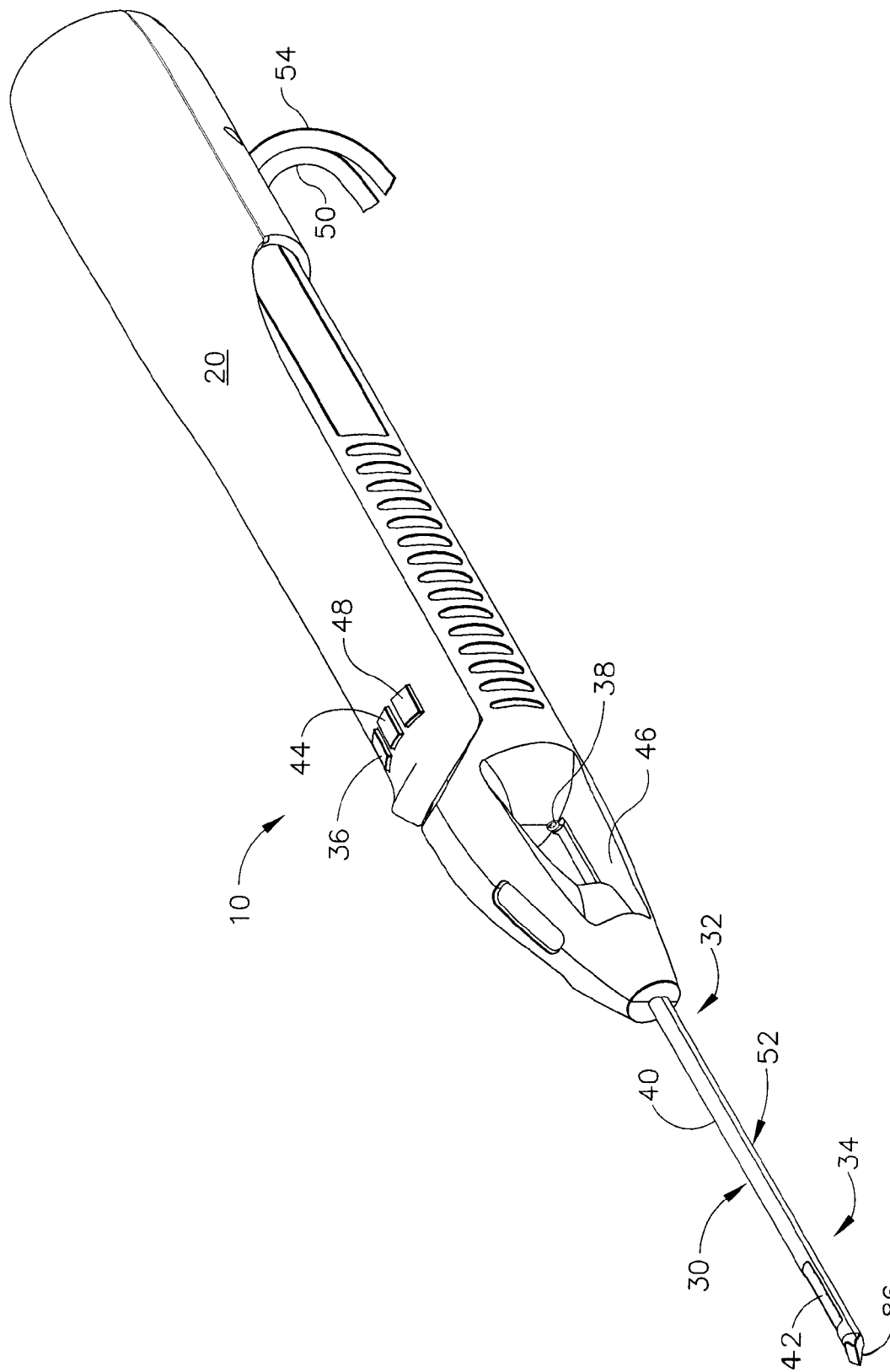
FIG. 1 is an isometric view of a hand-held vacuum-assisted biopsy device including a needle assembly manufactured according to one version of the process.

FIG. 1 shows a hand-held vacuum-assisted biopsy device 10 comprising a handle 20 detachably connected to a needle assembly 30 having a proximal portion 32 and a distal portion 34 manufactured according to a version of the process of the current invention. Together, they constitute a lightweight, ergonomically-shaped, hand-manipulated biopsy device 10. In one aspect, needle assembly 30 may be part of a disposable probe that may mount on handle 20. In one aspect, hand-held biopsy device 10 may be used in conjunction with an ultrasound to guide needle assembly 30. Since handle 20 may be manipulated by the operator's hand, the operator may steer needle assembly 30 with great freedom towards the tissue mass of interest. The surgeon has tactile feedback while doing so and may therefore ascertain to a significant degree the density and hardness of the tissue being encountered. In addition, handle 20 may be held approximately parallel to the chest wall of a patient for obtaining tissue portions closer to the chest wall than may be obtained when needle assembly 30 is attached to another type of device. Alternatively, needle assembly 30 may be attached to an electromechanical arm, a platform, a table or other suitable support. Such alternative mountings may be used in conjunction with applications in which the needle assembly is guided by stereotactic (x-ray) or MRI modalities.

As controls for obtaining a tissue sample, handle 20 may include a forward button 36 which may be used to move a cutter 38 distally through a cutter lumen 40 to sever a sample of suspicious tissue collected in a tissue-receiving port 42. Handle 20 may further include a reverse button 44 which may be used to move cutter 38 proximally through cutter lumen 40, thereby moving the tissue sample in port 42 to a tissue collection surface 46. A vacuum button 48 on handle 20 may be used to open or close a first vacuum line 50 for communicating suction to a vacuum lumen 52 so as to cause tissue to become disposed within port 42 and a second vacuum line 54 for communicating axial suction to cutter 38 to aid in withdrawal of a severed tissue sample.

Figure 2:
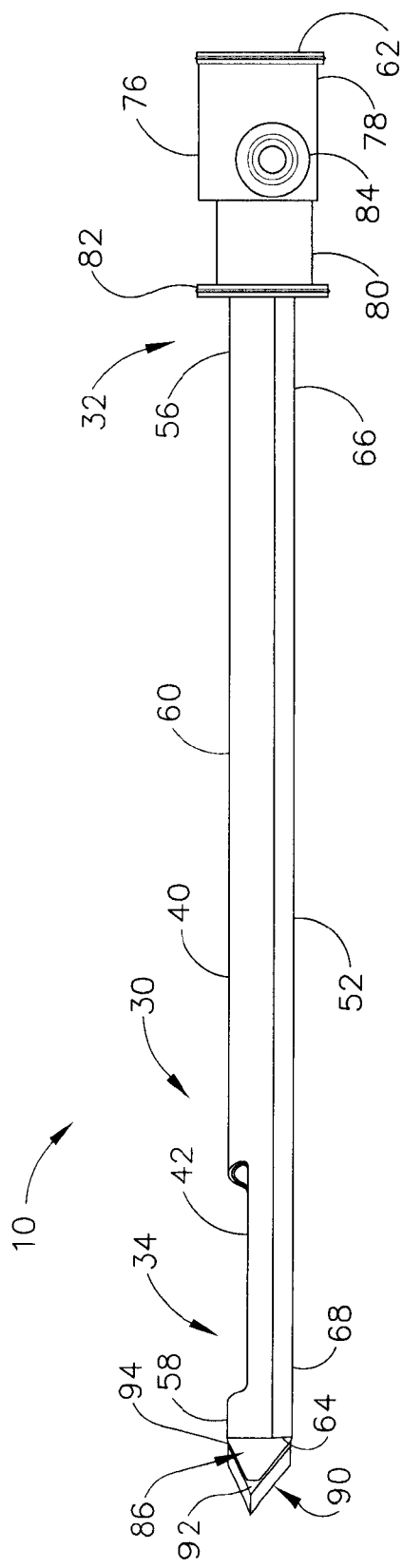
FIG. 2 is a side view of a needle assembly manufactured according to one version of the process.
Figure 3:
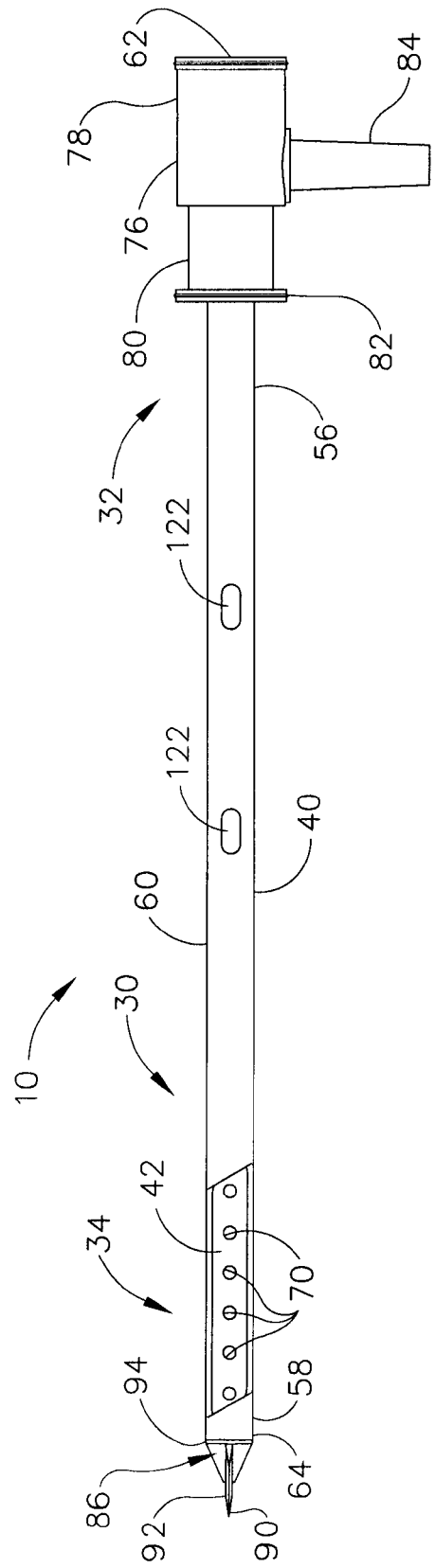
FIG. 3 is a top view of a needle assembly manufactured according to one version of the process.

Referring now to FIGS. 2 and 3, a needle assembly 30 made by one version of the process of the current invention for use with a biopsy device 10 is illustrated. Cutter lumen 40 may comprise a proximal portion 56 and a distal portion 58. Cutter lumen 40 forms a smooth, uninterrupted passage for receiving cutter 38 (not shown in FIGS. 2-3) such that it may be advanced through the proximal portion 56 of cutter lumen 40 to the distal portion 58. Tissue-receiving port 42 may be formed in an exterior surface 60 of cutter lumen 40. Port 42 may be located on the distal portion 58 of cutter lumen 40. Cutter lumen 40 may also comprise an open proximal end 62 and an open distal end 64.

Vacuum lumen 52 may comprise a proximal portion 66 and a distal portion 68. In one version, cutter lumen 40 may be oriented above vacuum lumen 52. A vacuum source (not pictured) may be attached to vacuum lumen 52, possibly at proximal portion 66 thereof, via first vacuum line 50.

Figure 6:
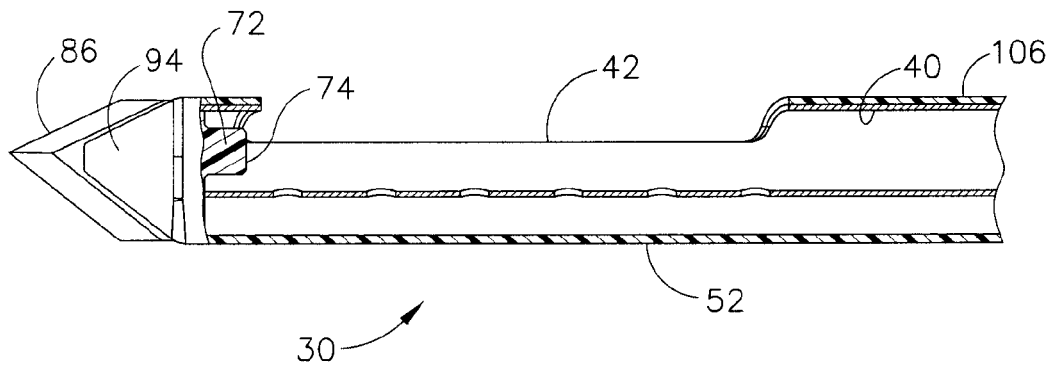
FIG. 6 is a section view of a cutter lumen and cutter stop manufactured according to one version of the process.
Figure 7:
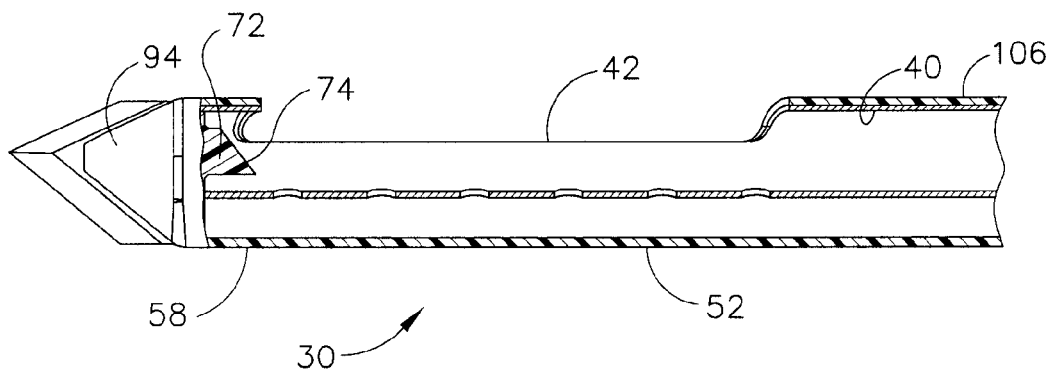
FIG. 7 is a section view of a cutter stop manufactured according to one version of the process.
Figure 11:
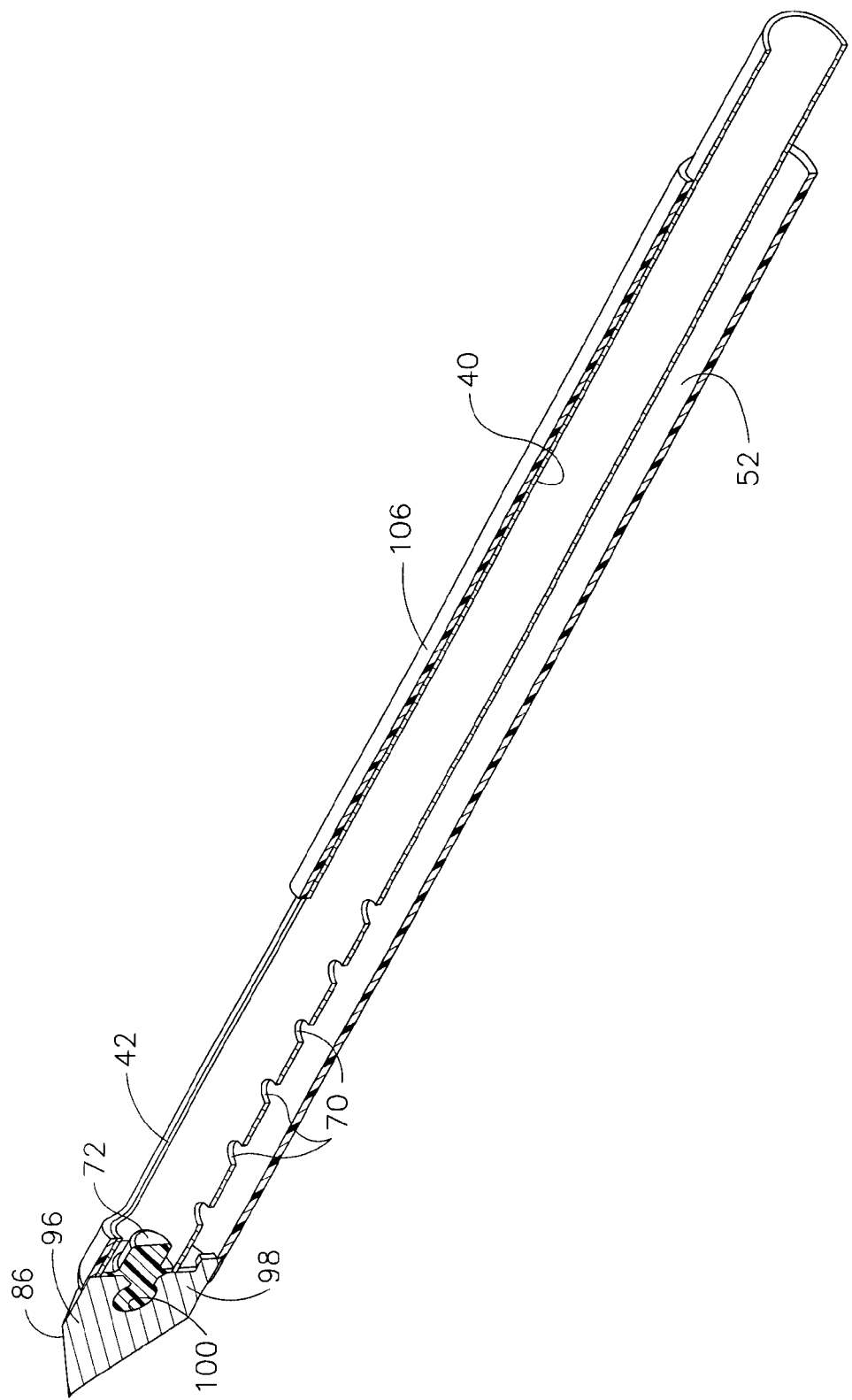
FIG. 11 is a partial sagittal cross-sectional view of a needle assembly manufactured according to one version of the process.

The needle assembly 30 may also include one or more passages, also called interlumen vacuum holes 70, between cutter lumen 40 and vacuum lumen 52. When the vacuum source is activated, thereby providing suction in vacuum lumen 52, interlumen vacuum holes 70 allow that suction to be communicated into cutter lumen 40. As best illustrated in FIGS. 3 and 11, the interlumen vacuum holes 70 may be located between cutter lumen 40 and vacuum lumen 52 opposite the tissue-receiving port 42. As illustrated in FIG. 6, a cutter stop 72 may also be located in cutter lumen 40 distally of tissue-receiving port 42. A face 74 of cutter stop 72 may provide a cutting surface for severing a tissue sample. Face 74 of cutter stop 72 may be designed to match the leading profile of cutter 38 (FIGS. 6 and 7). Depending on the means used to advance cutter 38, cutter stop 72 may also provide tactile feedback to a surgeon once cutter 38 comes into contact with cutter stop 72 after a sample has been severed. However, if, as known in the art, a computer software program is used to control advancement of cutter 38, the surgeon will not be provided with tactile feedback by contact between cutter 38 and cutter stop 72.

As illustrated in FIG. 2, a hub 76 having a proximal portion 78 and a distal portion 80 may be located on proximal portion 32 of needle assembly 30. Hub 76 assists in mounting needle assembly 30 to handle 20 or other any other suitable support. Hub 76 may detachably mount on handle 20 in order to allow disposable needle assembly 30 to be removed from the multiple-use handle 20 after surgery. Hub 76 may also include a flange 82 on its distal portion 80. Flange 82 may snap into a rib or similar retaining element (not shown) of handle 20 or another suitable support. Hub 76 may also include a vacuum manifold 84 that provides a connection between the vacuum source and vacuum lumen 52. Hub 76 may also allow second vacuum line 54 to connect with cutter 38 so that axial suction may be communicated to cutter 38.

In one aspect consistent with the process of the current invention, a distal tissue-piercing tip 86 having a proximal portion 88 and a distal portion 90 may be disposed on distal portion 34 of needle assembly 30. As best pictured in FIGS. 4 and 5, distal portion 90 of distal tissue-piercing tip 86 may include a cutting edge 92 of sufficient sharpness to cut through human tissue and thereby aid in moving needle assembly 30 adjacent to the tissue of interest. The junction of piercing tip 86 and cutter lumen 40 may include a tapered profile 94 therebetween that further assists needle assembly 30 in moving smoothly through a patient's tissue.

Piercing tip 86, particularly the distal portion 90, may comprise a substantially flat blade formed of any suitable material. Piercing tip 86 may also include tabs 96, 98 (FIGS. 4, 5, 11) on proximal portion 88 thereof to aid in the attachment of piercing tip 86 to cutter lumen 40. Tab 96 may be located above tab 98. In one version, tab 98 extends further toward proximal end 62 of cutter lumen 40 than does tab 96 for reasons addressed below. Piercing tip 86 may also include an opening 100, to aid in formation of tapered profile 94, which is also discussed in more detail below.

In operation, needle assembly 30 may be inserted into a small incision in the body. When utilized, tissue-piercing tip 86 helps needle assembly 30 penetrate through tissue until distal portion 34 of needle assembly 30 is located adjacent the tissue of interest. Piercing tip 86, along with tapered profile 94, may help to minimize tissue drag experienced during insertion and extraction of needle assembly 30. Once needle assembly 30 is properly positioned relative to the tissue of interest, vacuum suction may be applied to vacuum lumen 52 via first vacuum line 50.

Suction may be communicated from vacuum lumen 52 to cutter lumen 40 via the interlumen vacuum holes 70. The suction inside cutter lumen 40 actively pulls suspicious tissue into tissue-receiving port 42. Once the suspicious tissue has been drawn into cutter lumen 40 through port 42, the surgeon may advance cutter 38 in the distal direction until a sample is severed from the suspicious tissue. Cutter stop 72 may be located in cutter lumen 40 distally of tissue-receiving port 42 to provide a cutting surface to aid cutter 38 in severing a sample of suspicious tissue. Once the sample has been severed, cutter 38 may contact cutter stop 72. As mentioned above, depending on the means used to advance cutter 38 through cutter lumen 40, contact between cutter 38 and cutter stop 72 may provide tactile feedback to the surgeon, indicating that a sample has been obtained and that cutter 38 may be withdrawn toward proximal end 62 of cutter lumen 40. Once cutter 38 contacts cutter stop 72, needle assembly 30 may be repositioned in the patient's body (e.g., rotated, longitudinally translated) in order to obtain another sample.

As mentioned above, cutter 38 may be attached to second vacuum line 54, thereby providing cutter 38 with axial suction. After a sample has been obtained, and before a second sample is drawn into port 42, axial suction, if utilized, may assist cutter 38 in pulling the sample through cutter lumen 40 as cutter 38 is withdrawn. Once cutter 38 has been withdrawn from cutter lumen 40, the sample may be cleared from cutter 38 onto the tissue collection surface 46 located on handle 20 or platform. At that point, another sample may be obtained by applying vacuum to draw a sample into port 42 and advancing cutter 38 to sever the sample. This procedure may be repeated until the desired number of samples has been acquired.

In one aspect consistent with the process of the current invention, cutter lumen 40 may comprise a preformed tube open at each end and cut to the desired length of needle assembly 30. The preformed tube may be advantageously straight and round for receiving cutter 38. The material of the preformed tube may be rigid to allow insertion of needle assembly 30 through tissue with minimal deflection. In one version, cutter lumen 40 may be made of metal. More particularly, cutter lumen 40 may be made of stainless steel. Cutter lumen 40 may also be made from other suitable materials, including but not limited to titanium, titanium alloy, aluminum, or aluminum alloy. Alternatively, cutter lumen 40 may be made from nonmetallic materials having structural characteristics sufficient to allow a coating of material to be applied over cutter lumen 40 and having the strength and rigidity characteristics sufficient to withstand the force experienced by cutter lumen 40 when it is pressed through human tissue.

Tissue-receiving port 42 and interlumen vacuum holes 70 may be cut into the preformed tube comprising cutter lumen 40. As shown in FIG. 3, the distal and proximal edges of port 42 may be cut on an angle relative to the longitudinal edges of port 42. The angling of these edges can produce a scissoring effect as needle assembly 30 is pushed through tissue, aiding in positioning the device 10. In addition, a pair of notches 101, 102 (FIG. 8) may be cut into distal end 64 of the preformed tube comprising cutter lumen 40 to provide points of attachment for piercing tip 86.

Piercing tip 86 may be formed of a material providing sufficient strength and rigidity to allow it to move through tissue with minimal deflection. In one version, tip 86, including the above-described features included thereon, may be stamped from metal sheet stock. More particularly, the metal may be 440A stainless steel. However, other suitable materials may be used, including but not limited to titanium, titanium alloy, aluminum, or aluminum alloy. Non-metallic materials, such as MRI compatible resins, including but not limited to Ultem and Vectra, may be used to form tip 86. Likewise, tip 86 may also be formed from ceramics or glass. By stamping piercing tip 86 out of metal sheet stock, cutting edge 92 may be sharpened prior to attachment of tip 86 to cutter lumen 40. Cutting edge 92 may be sharpened after formation of tip 86 by grinding perpendicular to cutting edge 92, which is sometimes thought to be advantageous in producing a sharp cutting surface. Alternatively, cutting edge 92 may be sharpened by any other suitable method known in the art.

Piercing tip 86 may be attached to cutter lumen 40. In one version, piercing tip 86 may be welded to cutter lumen 40. More particularly, piercing tip 86 may be laser welded to cutter lumen 40. In one version, piercing tip 86 may be welded to cutter lumen 40 at two preformed locations. Tabs 96, 98 of piercing tip 86 may each be welded inside the notches 101, 102 of cutter lumen 40. Alternatively, piercing tip 86 may be attached to cutter lumen 40 through any suitable method known in the art that provides satisfactory strength of attachment between tip 86 and cutter lumen 40, including but not limited to adhesive, press-fit, or screws.

Other features of needle assembly 30 may be formed by applying a coating of material over cutter lumen 40. The coating of material may be applied to cutter lumen 40 as a liquid, and then hardened to the necessary rigidity for use in the human body after formation of the desired features thereon. In one version depicted in FIG. 9, the coating of material may be applied to cutter lumen 40 by injection molding. In this version, a mold 103 is designed such that the injected material may flow into predetermined cavities and form the desired features over cutter lumen 40, including but not limited to vacuum lumen 52 and hub 76. The gates (not pictured) through which the material is injected into the mold may be located along the mold part line, shown as $P_L$ in FIG. 9. Further, the gates may be located in the mold 103 underneath cutter lumen 40.

In this version, when the material is injected into the mold 103, it may form an outer sheath 106 over cutter lumen 40, as well as tapered profile 94 between piercing tip 86 and cutter lumen 40 (FIGS. 6, 7, 10, 11). To assist in formation of tapered profile 94, piercing tip 86 may include opening 100 (FIG. 4) through which the injected material may flow. Flow of injected material through opening 100 from each side of tip 86 may strengthen attachment of the injected material to piercing tip 86.

The mold 103 may also be shaped so that the applied material forms hub 76, flange 82, and vacuum manifold 84 over proximal portion 56 of cutter lumen 40. The mold 103 may also be designed so that hub 76 extends past proximal end 62 of cutter lumen 40 in order to facilitate the mounting of needle assembly 30 to handle 20 or another suitable support. Alternatively, hub 76, including flange 82 and vacuum manifold 84 may be formed separately from the remainder of needle assembly 30 and be attached by gluing, press-fitting or any other suitable method known in the art.

Referring to FIG. 9, prior to application of the coating of material, a slide 108 may be placed along exterior surface 60 of cutter lumen 40, substantially parallel to the longitudinal axis thereof. More particularly, slide 108 may be placed on the underside of exterior surface 60. The material then coats cutter lumen 40 and slide 108, forming vacuum lumen 52 substantially parallel to the longitudinal axis of cutter lumen 40. Slide 108 also serves to prevent the applied material from blocking interlumen vacuum holes 70. The mold 103 may also be designed so that slide 108 may be placed in alternate locations in order to orient vacuum lumen 52 above or to either side of cutter lumen 40, so long as at least one interlumen vacuum hole 70 is present between vacuum lumen 52 and cutter lumen 40 to allow suction to be communicated therebetween.

While use of slide 108 is one process for forming vacuum lumen 52 in the coating of material applied over cutter lumen 40, it is recognized that other methods of forming vacuum lumen 52 in the coating of material are also possible. For example, vacuum lumen 52 could be drilled out of the coating of material after the material reaches sufficient hardness.

As shown in FIG. 10, in one version consistent with the invention, the coating of material provides the combined cutter lumen 40 and vacuum lumen 52 with an egg-shaped frontal cross-section 110. During surgery, cross-section 110 promotes efficient motion of the needle assembly 30 through tissue. However, it is recognized that the application of a coating of material to cutter lumen 40 may provide needle assembly 30 with cross-sections of various shapes that are consistent with the process of the current invention. Further, as illustrated in FIGS. 9 and 10, slide 108 may comprise a scoop-shaped cross-section 111 that provides vacuum lumen 52 with a generally scoop-shaped frontal cross-section 112. While this is helpful in providing the combined cutter lumen 40 and vacuum lumen 52 with the egg-shaped frontal cross-section 110 described above, vacuum lumen 52 and slide 108 could comprise various frontal cross-sections that are consistent with the process of the current invention. For instance, slide 108 could have a circular frontal cross-section, thus providing vacuum lumen 52 with a circular frontal cross-section.

Figure 4:
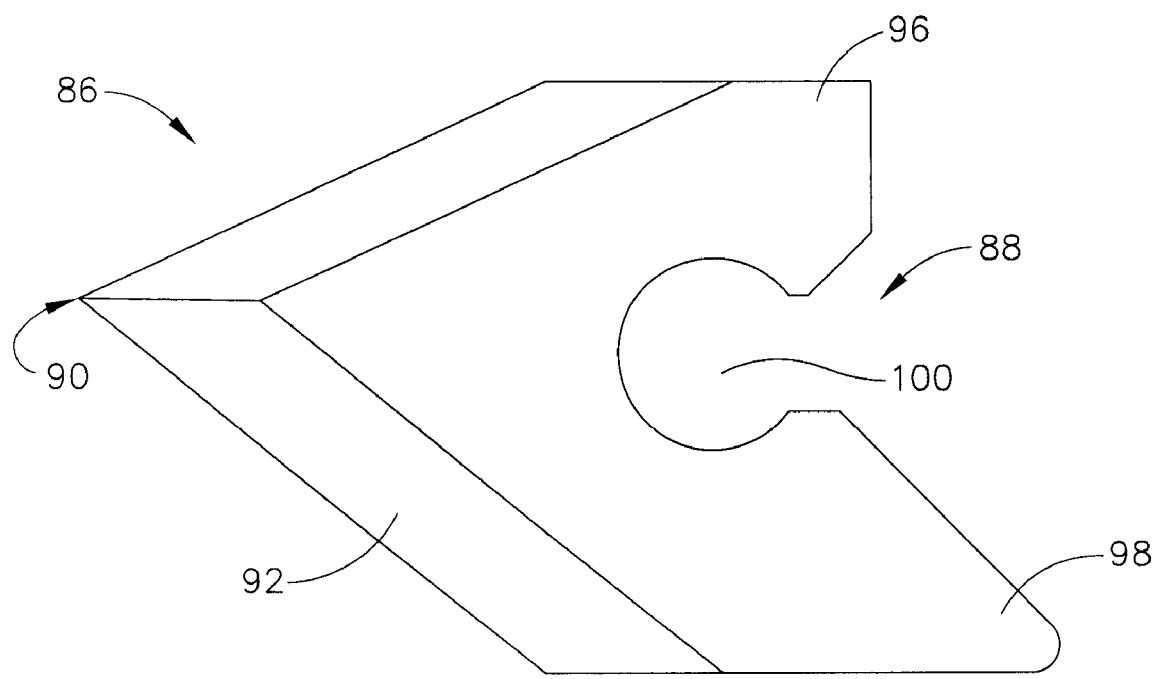
FIG. 4 is a side view of a distal tissue-piercing tip manufactured according to one version of the process.
Figure 5:
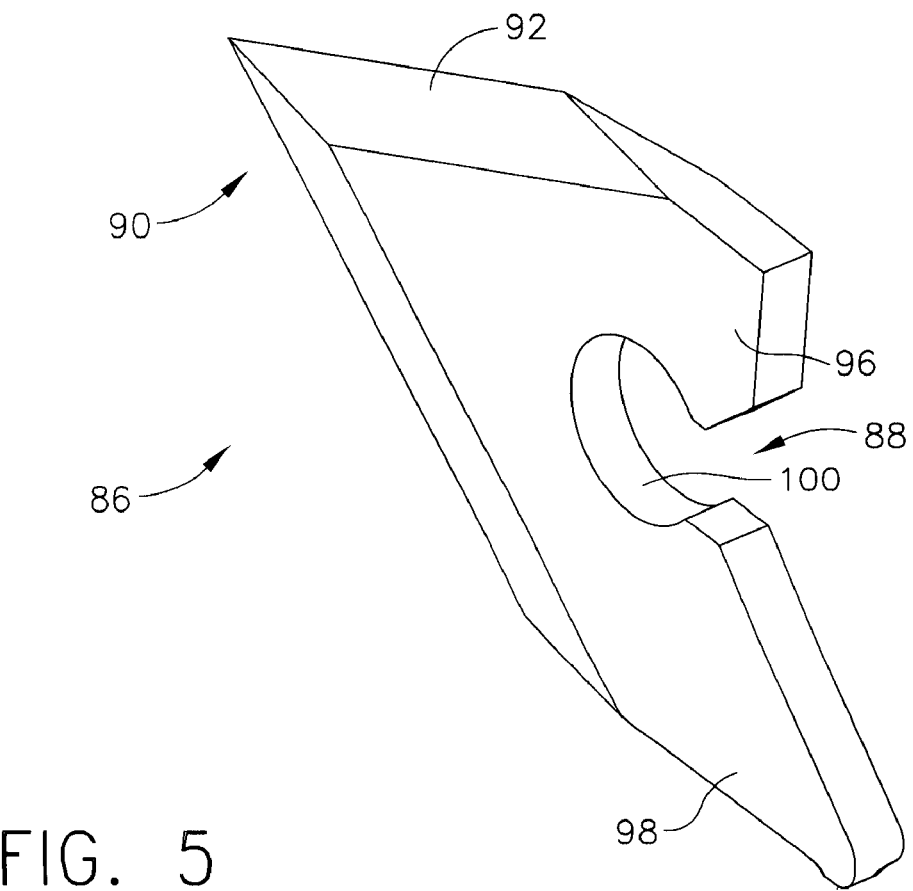
FIG. 5 is an isometric view of a distal tissue-piercing tip manufactured according to one version of the process.

As shown in FIGS. 4 and 5, tab 98 on piercing tip 86 may be elongated and slope downward in the proximal direction. In addition to serving as a point of attachment for welding piercing tip 86 to cutter lumen 40, tab 98 may also align and help hold slide 108 in place during molding.

Prior to application of the material to cutter lumen 40, a slide 112 (FIG. 9) may be inserted into tissue-receiving port 42. Slide 112 prevents any of the applied material from entering port 42.

Figure 8:
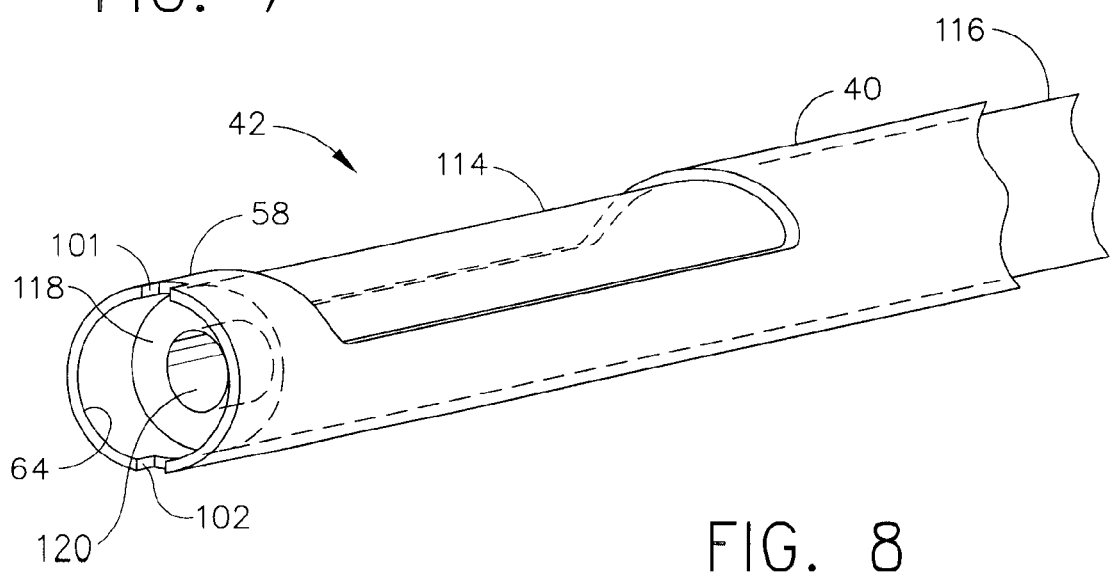
FIG. 8 is a partial view of a cutter lumen and axial slide according to one version of the process.

Referring now to FIGS. 8 and 9, an axial slide 114 having a proximal end 116 and a distal end 118 may be inserted into open proximal end 62 of cutter lumen 40 prior to application of the coating of material. Axial slide 114 prevents the applied material from entering proximal end 62 of cutter lumen 40. Further, axial slide 114 may be of a predetermined length such that distal end 118 extends into cutter lumen 40 distally of tissue-receiving port 42 but does not reach open distal end 64 of cutter lumen 40. Distal end 118 of slide 114 may further comprise an indentation 120. Piercing tip 86 may be attached to distal end 64 of cutter lumen 40 in a manner that does not prevent material from flowing into open distal end 64 during application of the material over cutter lumen 40. Accordingly, during the application process, material flows into open distal end 64 of cutter lumen 40 and into indentation 120 in axial slide 114, thereby forming cutter stop 72 in cutter lumen 40 distally of tissue-receiving port 42.

Additionally, in one version of the present invention, one or more slides may be placed against exterior surface 60 of cutter lumen 40 in order to hold cutter lumen 40 in position while the material is applied over cutter lumen 40 and prevent deformation due to the pressure of the applied material against exterior surface 60. As a result, outer sheath 106 may include windows 122 (FIG. 3) through which cutter lumen 40 is exposed.

The injected material may be selected from materials including, but not limited to, plastics, thermoplastics, thermoresins, and polymers. For instance, the molded features may be formed of a liquid crystal polymer or a glass reinforced polymer. One suitable material is a glass reinforced liquid crystal polymer such as VECTRA A130 available from Ticona Corp. In one version, the injected material may have a melt flow index of at least about 10 grams/minute, more particularly at least about 15 grams/minute. Without being limited by theory, such a mold flow index is thought to be beneficial for molding relatively long, thin-walled cross-sections.

While various versions of the present invention have been shown and described herein, it will be obvious to those skilled in the art that such alternatives are provided by way of example only. Numerous variations, changes, and substitutions will now occur to those skilled in the art without departing from the present invention. Additionally, each component or element may be described in terms of a means for performing the component's function. Accordingly, it is intended that the invention be limited only by the spirit and scope of the appended claims.

What is claimed is:

1. A process of manufacturing a biopsy needle assembly comprising:
    forming an aperture for receiving tissue to be sampled in an exterior surface of an elongated tube for receiving a cutter and having a proximal portion and a distal portion;
    attaching a tissue-piercing tip to said distal portion of said elongated tube;
    forming a hole in said exterior surface of said elongated tube; and
    applying a coating of material over said elongated tube to form a lumen for receiving vacuum on said exterior surface of said elongated tube, wherein said hole in said exterior surface of said elongated tube provides communication between an interior of said elongated tube and an interior of said lumen, wherein application of said coating of material forms a tapered profile between said tissue-piercing tip and said elongated tube.

2. The process of claim 1, further comprising stamping said tissue-piercing tip out of metal sheet stock prior to attaching said tissue-piercing tip to said elongated tube.

3. The process of claim 1, wherein said tissue-piercing tip comprises an opening through which said coating of material may flow.

4. The process of claim 1, further comprising placing said elongated tube in a mold, wherein said coating of material is applied to said elongated tube by injection molding.

5. The process of claim 4, further comprising placing a lumen slide against said exterior surface of said elongated tube before said coating of material is injected into said mold, wherein said coating of material flows over said elongated tube and said lumen slide to form said vacuum lumen.

6. The process of claim 5, wherein said lumen slide covers said hole in said exterior surface of elongated tube so that said coating of material does not block said hole.

7. The process of claim 4, further comprising inserting an aperture slide into said aperture in said elongated tube before said coating of material is injected into said mold to prevent said coating of material from entering said aperture.

8. The process of claim 4, further comprising inserting an elongated tube slide comprising a distal end and a proximal end through a proximal end of said elongated tube before said coating of material is injected into said mold.

9. The process of claim 8, further comprising placing said elongated tube slide into said elongated tube distally of said aperture before said coating of material is injected into said mold, wherein said distal end of said elongated tube slide further comprises a cutter stop mold such that said coating of material forms a cutter stop in said elongated tube located distally of said aperture.

10. The process of claim 1, wherein said coating of material comprises a liquid crystal polymer.

11. The process of claim 1, wherein said coating of material has a melt flow index of at least 15 grams/minute.

12. The process of claim 1, wherein application of said coating of material forms a mounting component having a proximal end and a distal end on said proximal portion of said elongated tube, wherein said distal end of said mounting component includes a flange.

13. The process of claim 12, wherein said mounting component is adapted to allow communication between a cutter and a vacuum source.

14. The process of claim 1, wherein application of said coating of material forms a vacuum manifold on said needle, said vacuum manifold having a first opening in communication with said lumen and a second opening for communication with a vacuum source.

15. The process of claim 1, wherein said coating of material forms a substantially egg-shaped frontal cross-section for a distal portion of said needle assembly.

16. The process of claim 1, further comprising placing a support against said exterior surface of said elongated tube before application of said coating of material to minimize deflection of said elongated tube during application of said coating of material.

17. A process of manufacturing a biopsy needle assembly comprising:
    forming an aperture for receiving tissue to be sampled in an exterior surface of an elongated tube for receiving a cutter and having a proximal portion and a distal portion;
    forming a hole in said exterior surface of said elongated tube; and
    placing said elongated tube in a mold and injecting said mold with a material, wherein said mold is configured such that said material forms a lumen for receiving vacuum on said exterior surface of said elongated tube, wherein said hole in said exterior surface of said elongated tube provides communication between an interior of said elongated tube and an interior of said lumen, wherein said material forms a substantially egg-shaped frontal cross-section for a distal portion of said needle assembly.

18. A process of manufacturing a biopsy needle assembly comprising:
    placing a cutter tube comprising a port adapted to receive a tissue sample, and further comprising a cutter lumen adapted to receive a cutter, in a mold;
    attaching a tissue-piercing tip to a distal portion of said cutter tube;
    injecting a material in a liquid state into said mold;
    cooling said material in order to convert it to a solid state;
    wherein said mold is configured to cause said material to form a lumen for receiving vacuum on an exterior surface of said cutter tube;
    wherein further said lumen for receiving vacuum is in communication with said cutter lumen;
    wherein further said tissue-piercing tip comprises an openin through which said material may flow.

* * * * *

UNITED STATES PATENT AND TRADEMARK OFFICE
CERTIFICATE OF CORRECTION

Page 1 of 1

PATENT NO. : 7,895,725 B2
APPLICATION NO. : 12/437961
DATED : March 1, 2011
INVENTOR(S) : Andrew T. Beckman et al.

It is certified that error appears in the above-identified patent and that said Letters Patent is hereby corrected as shown below:

Column 10, Claim 18, lines 60-61, reads "...an openin..."; which should be deleted and replaced with "...an opening..."

Signed and Sealed this
Nineteenth Day of April, 2011

David J. Kappos
*Director of the United States Patent and Trademark Office*